United States Patent
Rongione et al.

(10) Patent No.: US 6,897,327 B2
(45) Date of Patent: May 24, 2005

(54) MANUFACTURE OF CONJUGATED LINOLEIC SALTS AND ACIDS

(75) Inventors: Joseph C. Rongione, Highlands, NJ (US); Jenifer Heydinger Galante, Oakland, NJ (US); Steven L. Clauss, Manville, NJ (US); Randal J. Bernhardt, Antioch, IL (US); Phouvieng Xayariboun, North Aurora, IL (US)

(73) Assignee: Stepan Company, Northfield, IL (US)

( * ) Notice: Subject to any disclaimer, the term of this patent is extended or adjusted under 35 U.S.C. 154(b) by 0 days.

(21) Appl. No.: 10/434,011

(22) Filed: May 8, 2003

(65) Prior Publication Data

US 2004/0225141 A1 Nov. 11, 2004

(51) Int. Cl.$^7$ .............................................. C07C 51/347
(52) U.S. Cl. ....................................... 554/126; 554/156
(58) Field of Search ................................ 554/126, 156

(56) References Cited

U.S. PATENT DOCUMENTS

| | | |
|---|---|---|
| 3,162,658 A | 12/1964 | Baltes et al. |
| 3,984,444 A | 10/1976 | Ritz et al. |
| 4,185,027 A | 1/1980 | Logan |
| 5,872,289 A | 2/1999 | Appleby et al. |
| 6,015,833 A | 1/2000 | Saebo et al. |
| 6,060,514 A | 5/2000 | Jerome et al. |
| 6,160,140 A | 12/2000 | Bhaggan et al. |
| 6,225,486 B1 | 5/2001 | Saebo et al. |
| 6,333,353 B2 | 12/2001 | Saebo et al. |
| 6,420,577 B1 * | 7/2002 | Reaney et al. ............... 554/126 |
| 6,743,931 B2 * | 6/2004 | Sæbo et al. ................. 554/126 |
| 2004/0058998 A1 | 3/2004 | Saebo et al. |
| 2004/0225142 A1 * | 11/2004 | Saebo et al ................. 554/126 |

FOREIGN PATENT DOCUMENTS

| | | |
|---|---|---|
| GB | 1589314 | 10/1977 |
| WO | WO 9707187 | 2/1997 |
| WO | WO 0114304 | 1/2001 |

* cited by examiner

*Primary Examiner*—Deborah D. Carr
(74) *Attorney, Agent, or Firm*—McAndrews, Held & Malloy Ltd.

(57) ABSTRACT

A process to manufacture conjugated linoleic acid (CLA)-containing materials such as conjugated linoleic salts and acids that are enriched in desirable cis-9, trans-11- and trans-10, cis-12-CLA isomers and are low in certain undesirable isomers. The process generally entails isomerization of an alkyl ester of a linoleic acid-containing material at a temperature typically between about 90 to 140° C. to effectuate conjugation of the double bonds, followed by saponification of the resultant CLA-containing fatty acid ester to produce a CLA-containing fatty acid salt, optionally followed by neutralization of the CLA-containing fatty acid salt with an acid source to produce a CLA-containing fatty acid.

28 Claims, No Drawings

MANUFACTURE OF CONJUGATED LINOLEIC SALTS AND ACIDS

FIELD OF THE INVENTION

The invention relates to an improved process to manufacture conjugated linoleic salts and acids (CLAs) that decreases the formation of undesirable CLA isomers and unwanted ester side products, decreases processing time and decreases process waste streams. Other uses of the process of the invention include recovery of fatty acids from corresponding esters, isomerization of unsaturation in aliphatic compounds, and reduction of formation of undesired isomers in long chain polyunsaturates.

BACKGROUND OF THE INVENTION

Conjugated linoleic acids (CLAs) refers to a mixture of positional and geometric isomers of linoleic acids, which are unsaturated fatty acids considered essential to the human diet and found preferentially in dairy products and meat. CLAs have generated much interest in the academic and business communities because of its nutritional, therapeutic, and pharmacological properties. There are numerous known CLA compositions, along with various known routes to prepare such compositions. See, e.g., U.S. Pat. No. 6,420,577 (Reaney, et al.); U.S. Pat. No. 6,015,833 (Saebo, et. al.); U.S. Pat. No. 6,160,140 (Bhaggan, et. al.); U.S. Pat. No. 6,034,132 and U.S. Pat. No. 6,019,990 (both to Remmereit, J.); and U.S. Pat. No. 6,225,486 (Saebo, et. al.). CLAs have become biologically and commercially important, as they have been observed to inhibit mutagenesis and to provide unique nutritional value.

Typically, CLAs are a mixture of positional isomers of linoleic acid (C18:2) having conjugated double bonds. The cis-9, trans-11 and trans-10, cis-12 isomers are present in greatest abundance in typical CLA compositions, but it is not absolutely certain which isomers are responsible for the biological and heightened nutritional activity observed. It has been noted from labeled uptake studies that the 9,11 isomer appears to be somewhat preferentially taken up and incorporated into the phospholipid fraction of animal tissues, and to a lesser extent the 10,12 isomer. (See Ha, et al., Cancer Res., 50: 1097 (1991)).

The properties of unsaturated fatty acids and their derivatives can be altered by rearrangement, i.e., isomerization, of the structure of the double bond, either with respect to the steric position or the position in the carbon chain of the molecule of the fatty acid. As noted above, conjugated fatty acid derivatives are of great technical and commercial interest and, therefore, many attempts have been made to isomerize unconjugated fatty acids to conjugated ones. Without being bound by any particular theory, it is believed that such a shifting of the double bond is possible because the conjugated form has a lower state of energy than the unconjugated form.

Previously known routes to produce conjugated unsaturated compounds include hydrogenation of fats using a variety of catalysts. These routes, however, often lead to incomplete isomerization and unwanted side reactions, such as polymerization and intramolecular cyclization. Other known routes include isomerization with an excess of alkali metal hydroxide in an aqueous or alcoholic medium, which leads to a quantitative isomerization. However, this route suffers from the limitation that a considerable excess of alkali metal hydroxide must be used, so that the conjugated fatty acids or fatty acid compounds are obtained in the form of their alkali soaps and have to be recovered and isolated accordingly. These techniques differ in the use of a particular solvent, temperature and pressure. See, e.g., U.S. Pat. No. 3,162,658 (Baltes, et. al.).

The rearrangement of the double bonds of linoleic acids to conjugated positions has been shown to occur during treatment with catalysts such as nickel or alkali at high temperatures, and during auto oxidation. Theoretically, eight possible geometric isomers of 9,11 and 10,12 octadecadienoic acid (c9, c11; c9, t11; t9, c11; t9, t11; c10, c12; c10, t2; t10, c12 and t10, t12) would result from the isomerization of c9, c12-octadecadienoic acid. Again, without being bound by any particular theory, a general mechanism for the isomerization of linoleic acids has been described by J. C. Cowan in JAOCS 72:492-99 (1950). The formation of certain isomers of CLAs is thermodynamically favored as described therein. The relatively higher distribution of 9,11 and 10,12 isomers apparently results from the further stabilization of the c9, t11 or t10, c12 geometric isomers.

U.S. Pat. No. 6,420,577 (Reaney, et al.) describe a process for making CLAs by reacting a linoleic acid-rich oil with a base, in the presence of a catalytic amount of such a base, in an aqueous medium via simultaneous saponification and quantitative isomerization. However, this process utilizes a heightened temperature (>170° C.). Higher temperatures lead to the formation of undesirable CLA isomers, including the trans, trans-CLA isomers.

U.S. Pat. No. 6,160,140 (Bhaggan, et al., the '140 patent) claims the conversion of a linoleic acid-containing oil, free fatty acid or alkyl ester to CLAs by treating it with a base in an alcohol solution, where the alcohol has at least 3 carbons and at least 2 hydroxyl groups. The preferred embodiment of the '140 patent is to use potassium hydroxide in propylene glycol. The use of solvent in the conjugation (isomerization) step gives rise to the potential formation of unwanted CLA-alcohol esters (e.g. CLA-propylene glycol esters).

U.S. Pat. No. 3,162,658 (the '658 patent) describes the use of alkali metal hydrocarbyl alcoholates or alkali metal amides to isomerize esters of unconjugated polyethylene acids such as linoleic acids. But it uses polar solvents for the isomerization step, which is undesirable. And the '658 patent also makes no mention of converting the resultant conjugated esters to the corresponding acids.

U.S. Pat. No. 3,984,444 (Ritz, et al., the '444 patent) describes the isomerization of an ester of an alcohol having 1 to 12 carbon atoms and an fatty acid having 10 to 24 carbon atoms and isolated double bonds to the corresponding compound having conjugated double bonds using alkaline metal alcoholates in strongly polar aprotic solvents. As noted above, the use of solvents in the conjugation step is undesirable. The '444 patent does not teach how to convert the resultant conjugated esters to the corresponding acids as well.

Typical procedures for the conversion of fatty acid methyl esters (FAME) to fatty acids (FA), such as those described in U.S. Pat. No. 4,185,027 and U.S. Pat. No. 5,872,289, involve the use of acidic catalysts. The use of such acidic catalysts is undesirable.

WO 01/14304 uses steam in the presence of a catalyst to directly hydrolyze FAME to FA. The reaction is carried out at a heightened temperature, which leads to the formation of undesirable CLA isomers, including the trans, trans-CLA isomers. Similarly, WO 97/07187 uses near critical temperatures and supercritical pressures to accomplish the transformation of FAME to FA.

GB 1589314 uses alkali metal hydroxides in alkyl nitrile solution for the conversion of FAME to FA.

As previously alluded to, CLAs have a wide variety of nutritional, therapeutic, and pharmacological uses. These uses include for example, body fat reduction, body weight reduction, increased muscle mass, increased feed efficiency, attenuated allergic reactions, prevention of weight loss due to immune stimulation, elevated CD-4 and CD-8 cells counts in animals, increased bone mineral content, prevention of skeletal abnormalities in animals and decreased blood cholesterol levels. The anticarcinogenic properties of CLA have been well documented. Administration of CLA inhibits rat mammary tumorigenesis, as demonstrated by Ha, et al., Cancer Res., 52: 2035s (1992). Ha, et al., Cancer Res., 50: 1097 (1990) reported similar results in a mouse forestomach neoplasia model. CLA has also been identified as a strong cytotoxic agent against target human melanoma, colorectal and breast cancer cells in vitro. A recent major review article confirms the conclusions drawn from individual studies. See Ip, Am. J. Clin. Nutr., 66 (6 Supp): 1523s (1997).

More recently, much attention has focused on CLA nutritively as a dietary supplement. CLA has been found to exert a profound generalized effect on body composition, in particular redirecting the partitioning of fat and lean tissue mass. See, e.g., U.S. Pat. No. 5,554,646 (Cook, et al.), which discloses a method utilizing CLA as a dietary supplement in various mammals, wherein a significant drop in fat content was observed with a concomitant increase in protein mass. See also, U.S. Pat. No. 5,428,072 (Cook, et al.), which disclosed that incorporation of CLA into animal feed (birds and mammals) increased the efficiency of feed conversion leading to greater weight gain in the CLA supplemented animals; the potential beneficial effects of CLA supplementation for food animal growers is apparent.

CLA is naturally occurring in foods and feeds consumed by humans and animals alike. In particular, CLA is abundant in products from ruminants. For example, several studies have been conducted in which CLA has been surveyed in various dairy products. Aneja, et al., J. Dairy Sci., 43: 231 (1990) observed that processing of milk into yogurt resulted in a concentration of CLA. Linoleic acid is an important component of biolipids, and comprises a significant proportion of triglycerides and phospholipids. Linoleic acid is known as an "essential" fatty acid, meaning that the animal must obtain it from exogenous dietary sources since it cannot be autosynthesized.

U.S. Pat No. 6,203,843 and U.S. Pat. No. 6,042,869 (both to Remmereit, J.) disclose bulk animal feeds containing CLA. U.S. Pat. No. 6,242,621 (Jerome et. al.) and U.S. Pat. No. 6,333,353 (Saebo, et al.) both disclose isomer enriched CLA compositions and methods of preparing such compositions.

The problem with most CLA products made by conventional approaches is their heterogeneity, and substantial variation in isoform from batch to batch. Considerable attention has been given to the fact that the ingestion of large amounts of hydrogenated oils and shortenings, instead of animal tallow, has resulted in a diet high in trans-fatty acid content For example, Holman, et al., PNAS, 88:4830 (1991) showed that rats fed hydrogenated oils gave rise to an accumulation in rat liver of unusual polyunsaturated fatty acid isomers, which appeared to interfere with the normal metabolism of naturally occurring polyunsaturated fatty acids. These concerns were summarized in an early Editorial in Am. J. Public Health, 84: 722 (1974).

Therefore, there exists a strong need for an improved process to produce a superior CLA composition, which is enriched with highly desired cis-9, trans-11- and trans-10, cis-12-CLA isomers, but which is low in certain undesirable CLA isomers and unwanted ester side products. Additionally, there is a need for an improved process to readily and economically prepare such CLA compositions in a safer and more environmental friendly way.

BRIEF SUMMARY OF THE INVENTION

CLAs made by conventional treatment of a linoleic oil (e.g. safflower, sunflower) or an alkyl linoleate composition with a basic catalyst such as potassium hydroxide contain relatively high levels of undesirable isomers (e.g., trans-11, trans-13; trans-8, trans-10-; trans-9, cis-11- and cis-10, trans-12-CLA). It has been surprisingly discovered that the inventive process described herein produces conjugated linoleic acid-containing fatty acids, which are enriched in desirable cis-9, trans-11 and trans-10, cis-12-CLA isomers, but contain very small amounts of undesirable isomers. It is an object of the present invention to provide a process to produce compositions containing high levels of desirable CLA isomers.

Compared with prior art, in the present invention, the isomerization step is performed at a lower temperature with minimal solvent, which improves both productivity and isomer ratio. The salt formation reaction of the saponification step is performed in a suitable medium at significantly lower temperature (about 75° C.) than the prior art (about 200° C.), which removes the need for a pressure vessel, improves process safety, decreases environmental hazards and preserves desirable product isomer ratios. Some of the salt is preformed and added to the reaction mixture, which significantly decreases the reaction time of the saponification step. Therefore, the present invention decreases the formation of undesirable CLA isomers, unwanted ester side products, decreases processing time and decreases process waste streams.

More specifically, the invention provides a process to prepare CLAs wherein an alkyl linoleate composition is treated with alkyl alcoholate at temperatures low enough to suppress formation of undesirable CLA isomers but sufficient to cause rearrangement of the double bonds. The preferred operating temperature range for this isomerization step is 80–140° C., and the preferred catalyst loading is 1–4% by weight based on the weight of the linoleic acid-containing material. After neutralization of the alkyl alcoholate catalyst, the alkyl CLA intermediate product is reacted with an alkali or alkaline earth hydroxide to form the metal salt of the CLA in a saponification step. The preferred hydroxide/ester ratio range is 1.05–2.5 and the preferred operating temperature range for the saponification step is 45–100° C. Thereafter, the CLA metal salt intermediate can be optionally neutralized with an acid source to yield a product CLA. The low temperature employed in the process of the invention (especially in the step of saponification) prohibits any further rearrangement of the CLA double bonds, so the desirable isomer distribution remains unchanged in the final conjugated linoleic acid product. Stated in another way, the low-temperature process of the invention for producing CLAs preserves the integrity of the conjugated double bonds and does not cause formation of undesirable isomers.

Another aspect of the invention provides a conjugated linoleic acid-containing material produced by the process described above, which is enriched in desirable cis-9, trans-11 (c9, t11) and trans-10, cis-12 (t10, c12) CLA isomers and contains very small amounts of undesirable isomers. In another aspect of the invention, the enriched t10, c12 and c9, t11-materials prepared by the inventive process may be incorporated into food products, including animal feeds and food for human consumption, or may be formulated with an excipient or oral delivery vehicle.

DETAILED DESCRIPTION OF THE INVENTION

Definitions And Conventions

As used herein, "conjugated linoleic acid" or "CLA" refers to any conjugated linoleic acid or octadecadienoic free fatty acid. It is intended that this term encompass and indicate all positional and geometric isomers of linoleic acid with two conjugated carbon-carbon double bonds any place in the molecule. CLA differs from ordinary linoleic acid in that ordinary linoleic acid has double bonds at carbon atoms 9 and 12. Examples of CLA include cis- and trans isomers ("E/Z isomers") of the following positional isomers: 2,4-octadecadienoic acid, 4,6-octadecadienoic acid, 6,8-octadecadienoic acid, 7,9-octadecadienoic acid, 8,10-octadecadienoic acid, 9,11-octadecadienoic acid and 10,12 octadecadienoic acid, 11,13 octadecadienoic acid. As used herein, "CLA" encompasses a single isomer, a selected mixture of two or more isomers, and a non-selected mixture of isomers obtained from natural sources, as well as synthetic and semi-synthetic CLA.

As used herein, it is intended that "esters" of CLA include any and all positional and geometric isomers of CLA bound through an ester linkage to an alcohol or any other chemical group, including, but not limited to physiologically acceptable, naturally occurring alcohols (e.g., methanol, ethanol, propanol). Therefore, an ester of CLA or esterified CLA may contain any of the positional and geometric isomers of CLA.

As used herein, it is intended that "triglycerides" of CLA contain CLA at any or all of three positions on the triglyceride backbone. Accordingly, a triglyceride containing CLA may contain any of the positional and geometric isomers of CLA.

It is intended that "undesirable isomers" of CLA include, but are not limited to c11, t13; t11, c13; t11, t13; c11, c13; c8, t10; t8, t10; c8, c10; and trans-trans isomers of octadecadienoic acid, and does not include t10, c12 and c9, t11 isomers of octadecadienoic acid. Undesirable isomers may also be referred to as "minor isomers" of CLA as these isomers are generally produced in low amounts when CLA is synthesized by alkali isomerization.

As used herein, "c" encompasses a chemical bond in the cis orientation, and "t" refers to a chemical bond in the trans orientation. If a positional isomer of CLA is designated without a "c" or a "t", then that designation includes all four possible isomers. For example, 10,12 octadecadienoic acid encompasses c10, t12; t10, c12; t10, t12; and c10, c12 octadecadienoic acid, while t10, c12 octadecadienoic acid or CLA refers to just the single isomer.

As used herein, the term "oil" refers to a free flowing liquid containing long chain fatty acids (including CLA) or other long chain hydrocarbon groups. The long chain fatty acids, include, but are not limited to the various isomers of CLA.

The fatty acid distribution was determined by gas chromatography (GC) using a Chrompack CP-Sil 88 capillary column, 100 m×0.25 mm, df=0.2 microns; helium carrier at approximately 1.0 mL/min. The following temperature parameters were used: injector 250° C.; detector 250° C.; oven temperature 75° C. (2.0 min); 5° C./min to 185° C. (30.0 min); 4° C./min to 225° C. (36.0 min).

Description of the Invention

This invention encompasses a process to produce a conjugated linoleic salt or acid product, comprising:

a) isomerization of an alkyl ester of a linoleic acid-containing fatty acid derived from a linoleic acid-containing oil to produce a conjugated linoleic acid-containing fatty acid ester;

b) saponification of the conjugated linoleic acid-containing fatty acid ester to produce a conjugated linoleic acid-containing fatty acid salt; and c) optionally, neutralization of the conjugated linoleic acid-containing fatty acid salt with an acid source to produce the product CLA.

Typically, the isomerization step is catalyzed by a base in a nonaqueous system, and the preferred catalyst is an alkali or alkaline earth alkoxide salt of an alkyl group alcohol (1–4 carbons). The preferred cation of the alkoxide salt catalyst is sodium (Na), potassium (K) or calcium (Ca), and the preferred catalyst loading is 1–7% by weight based on the weight of the linoleic acid-containing material. Preferably, the catalyst is delivered as a solid or as a solution in the conjugate alcohol of the alkoxide. The isomerization reaction is typically performed at or below 140° C., preferably between 90–130° C., and more preferably between 110–120° C. The catalyst is added to the alkyl ester at a preferred temperature of 140° C. or below.

The alkyl ester composition used in the process of the invention is derived from a suitable fatty oil. Such oils include, for example, those, which are naturally high in linoleic acid residues, such as sunflower oil, safflower oil, soybean oil, corn oil or a combination thereof. By linoleic acid residue is meant an ester material which has a fatty carbon chain length and isomer distribution to that resembling linoleic acid. These fatty oils are typically triglycerides which are wholly or substantially converted to an alkyl ester starting material, i.e. an alkyl linoleate rich material, prior to use in the inventive conjugation process. Typically, this preliminary alkylation is accomplished by known esterification routes using short chain $C_1$–$C_6$ alcohols or any other suitable alcohol. During this preliminary process, triglycerides are converted to the starting alkyl ester composition (rich in alkyl linoleate); this starting alkyl ester material may also contain small amounts of un-transesterified monoglycerides, diglycerides along with significant amount of glycerine. These non-alkyl linoleate materials are not critical to practicing the inventive conjugation process of the invention and generally do not interfere with the process.

Generally, any alkali or alkaline earth metal compound of any monohydric alcohol can be used as a catalyst for the isomerization step, for example, alkali or alkaline earth metal compounds of methyl alcohol, ethyl alcohol, propyl alcohol, or butyl alcohol and also alkali or alkaline earth metal amides. Cesium, rubidium, potassium, sodium, calcium, lithium, magnesium or zinc alcoholates may be utilized, along with mixtures of such alcoholates. Sodium, potassium or calcium alkoxide salts (1–4 carbons) are preferred. Alkali or alkaline earth metals, alkali or alkaline earth metal hydrides, and organic alkali or alkaline earth metal compounds, may be used so long as they react in the reaction mixture to form active catalysts such as alkali or alkaline earth metal alcoholates or alkali or alkaline earth metal amides. According to the invention the catalyst may be used in the amount of 1–7% by weight, based on the weight of the starting linoleic acid-containing material. Preferably, the amount of alkyl alcoholate used is 1.8–3% by weight, based on the weight of the starting linoleic acid-containing material.

Examples of alkyl alcoholates catalysts useful in carrying out the present invention are alcoholates of monohydric alcohols with 1–18 carbon atoms, of the alkali or alkaline earth metals such as alkali or alkaline earth metal alcoholates of methyl, ethyl, propyl, butyl, tertiary butyl, lauryl, stearyl, oleyl, benzyl alcohols, alkali or alkaline earth metal amides, and substances, such as alkali or alkaline earth metals, alkali or alkaline earth metal hydrides, and organic alkali or alkaline earth metal compounds, e.g. triphenyl sodium, which form in the reaction mixture the mentioned active isomerization catalysts. The alkali or alkaline earth metal alcoholates can be called alkali or alkaline earth metal hydrocarbyl alcoholates. The specific alcoholates set forth in this paragraph except that from benzyl alcohol can be termed as alkali or alkaline earth metal alkanolates.

In a preferred embodiment, no solvent is added for the isomerization step. The catalyst for the isomerization step may be added in solvent but the starting alkyl ester of a linoleic acid-containing material is not dissolved in a solvent. Relative to the ester quantity, the catalyst solvent is present in a minimal and negligible amount at any given time since the catalyst solvent is distilled from the reactor soon after it is added. By avoiding the use of solvent in the isomerization step, the potential formation of unwanted CLA-alcohol esters is eliminated.

However, a person of ordinary skill in the art would understand that the process of the invention can optionally, although less preferably, be carried out in the presence of solvents which do not interfere with the overall conjugation reaction. Examples of such optional solvents, which are used preferably in an amount of 10 to 50 percent based on the weight of the starting alkyl ester, are methyl, ethyl, isopropyl, butyl, amyl alcohol, pentane, hexane, heptane, heptylene-(1), octylene-1, benzene, toluene, and a combination thereof.

In the saponification step, the conjugated linoleic acid-containing fatty acid ester produced in the isomerization step reacts with an inorganic hydroxide or an alkyl ammonium hydroxide to produce a conjugated linoleic acid-containing fatty acid salt. The saponification step is typically performed between ambient temperature and 100° C., but the preferred operating temperature range is 45–100° C. The preferred cation of the inorganic hydroxide is sodium (Na), potassium (K) or calcium (Ca) and the preferred cation of the alkyl ammonium hydroxide is a symmetrical lower tetraalkyl (1–4 carbons) (tetramethyl, tetraethyl, tetrapropyl and tetrabutyl), benzyl trialkyl (1–4 carbons), dibenzyl dialkyl (1–4 carbons) or long chain alkyl (12–18 carbons) trialkyl (1–4 carbons) ammonium group. The preferred hydroxide/ester ratio is within the range of 1.05–2.5.

The saponification step can be performed in an aqueous, or nonaqueous aliphatic mono-alcohol, or mixed aqueous/alkyl mono-alcohol system. Examples of such solvents are, but not limited to, water, methanol, ethanol, isopropanol, butanol and a combination thereof.

In the optional neutralization step, a concentrated acid is added to the fatty acid salt solution to liberate the conjugated linoleic acids. Suitable acids for the neutralization can be selected from a group including, but not limited to sulfuric, phosphoric, hydrochloric, citric and oxalic acids.

The conjugated linoleic acid-containing product resulting from the inventive process, is enriched in desirable cis-9, trans-11 (c9, t11) and trans-10, cis-12 (t10, c12)-CLA isomers but contains very small amounts of undesirable isomers. It is a mixture (or a mixture of salts) of CLAs, linoleic acids and the other fatty acids found in the precursor source oil as described above. Preferably, the conjugated linoleic acid-containing product derived from the isomerization of sunflower oil contains approximately equal amounts of the c9, t11 and t10, c12 isomers.

Embodiments

In one embodiment, the saponification step is performed in a mixed aqueous/lower alkyl (1–4 carbons) mono-alcohol system at a temperature below 100° C. In another embodiment, the saponification step is performed in a non-aqueous aliphatic (1–4 carbons) mono-alcohol solvent at a temperature below 100° C. In both of these embodiments, the fatty acid salts can be isolated, for example, via filtration, prior to the optional neutralization step. And the preferred inorganic cation of the salts so collected is sodium (Na), potassium (K) or calcium (Ca).

In another embodiment, the saponification reaction is performed in an aqueous system at a temperature below 100° C. In this embodiment, a preformed alkali, alkaline earth or alkyl ammonium salt of the conjugated linoleic acid-containing fatty acid is present to increase the reaction rate of the saponification of the conjugated linoleic acid-containing fatty acid alkyl ester (1–4 carbons) in the aqueous system. The preferred cation of the preformed alkali or alkaline earth fatty acid salt is sodium (Na), potassium (K) or calcium (Ca). The preferred cation of the preformed alkyl ammonium salt is a symmetrical lower tetraalkyl (1–4 carbons), benzyl trialkyl (1–4 carbons), dibenzyl dialkyl (1–4 carbons) or long chain alkyl (12–18 carbons) trialkyl (1–4 carbons) ammonium group.

In one embodiment, the saponification step is effected by the use of a base consisting of an alkali, alkaline earth or alkyl ammonium cation and a hydroxide, bicarbonate or carbonate anion. The preferred cation is sodium (Na), potassium (K) or calcium (Ca), or a symmetrical lower tetraalkyl (1–4 carbons), benzyl trialkyl (1–4 carbons), dibenzyl dialkyl (1–4 carbons) or long chain alkyl (12–18 carbons) trialkyl (1–4 carbons) ammonium group.

In another embodiment, the conjugated linoleic acid-containing fatty acid (CLA) is generated from the soap solution resulting from the saponification step by reacting it with an acid source in a continuous neutralizing apparatus.

In still another embodiment, the alkali or alkaline earth salt of the conjugated linoleic acid-containing fatty acid resulting from the saponification step is refined by selective precipitation of the salts of saturated long chain fatty acids (14–20 carbons) from alcoholic or aqueous/alcoholic solutions before being neutralized. In this embodiment, preferably, the cation of the fatty acid salt is sodium (Na), potassium (K) or calcium (Ca), and the alcoholic solvents are selected from the group consisting of aliphatic short chain (1–4 carbons) mono-alcohols and a combination thereof.

Other Embodiments

In a method similar to that disclosed in U.S. Pat. No. 5,554,646 (Cook et al.), the invention contemplates the use of a CLA-containing material, produced by the inventive process, for reducing body fat in animals. The exact amount of CLA to be administered to reduce body fat depends upon the animal, the form of CLA employed, and the route of administration. The amount generally ranges from about 0.001 g/kg to about 1 g/kg of the animal's body weight. Pharmaceutical amounts will generally range from about 1,000 parts per million (ppm) to about 10,000 ppm of CLA of the human's diet. However, the upper limit of the amount to be employed is not critical because CLA is relatively nontoxic. CLA for this and other uses may also be derivatized in a variety of forms. These include nontoxic sodium or potassium salts of CLA in combination with a pharmaceutical diluent and active esters. CLA may also be incorporated directly into animal feed or food to be fed to a human so that CLA comprises approximately 0.01% to 2.0% or more by weight of the animal's or human's food. This embodiment also contemplates that supplementation of an animal's diet with CLA may serve to preserve body protein in an animal and to increase muscle protein in an animal.

In a method similar to that disclosed in U.S. Pat. No. 5,428,072 (Cook et al.), the invention contemplates the use of a CLA-containing material, produced by the inventive process, to enhance weight gain and feed efficiency in animals. Guidelines for amounts of CLA, produced by the inventive process, to be fed or included in the diet are identical to those disclosed in U.S. Pat. No. 5,554,646 (Cook, et al.).

In a method similar to that disclosed in a double blind study conducted in Norway by Erling Thom in 1997, the invention contemplates the use of a CLA-containing material, produced by the inventive process, to reduce body weight in humans. In a method similar to that disclosed in PCT Publication WO 97/46230, the invention contemplates the use of CLA, produced by the inventive process, for maintaining an existing level of body fat and/or body weight.

In a method similar to that disclosed in U.S. Pat. No. 5,585,400 (Cook et al.), the invention contemplates the use of a CLA-containing material, produced by the inventive process, for attenuating allergic reactions in animals mediated by Type I or TgE hypersensitivity by administering a diet containing such CLA. In accordance with this embodiment, the CLA produced by the inventive process may be administered in concentrations of about 0.1 to 1.0% to preserve numbers of white blood cells.

In another embodiment, a CLA-containing material prepared by the inventive process, may be used to enhance growth and prevent anorexia and weight loss due to immune stimulation (e.g., endotoxin exposure) and the adverse effects of catabolic hormones (e.g., IL-1) in a manner similar to that disclosed in U.S. Pat. No. 5,430,066 (Cook, et al.). Applicable dosage ranges are identical to those disclosed in U.S. Pat. No. 5,554,646 (Cook, et al.).

The invention encompasses methods of treating animals to maintain or elevate CD-4 and CD-8 cell levels and to prevent or alleviate the adverse effects on the animal caused by the production or exogenous administration of tumor necrosis factor (TNF) or by a virus consisting of administering to the animal a safe and effective amount of CLA, prepared by the inventive process, as generally disclosed in U.S. Pat. No. 5,674,901 (Cook et al.).

In a method similar to that disclosed in European Patent Application 779,033 A1 (Lievense, et al.), the invention contemplates the use of a CLA-containing material, produced by the inventive process, for improving blood lipid profile.

The invention contemplates the use of a CLA-containing material, produced by the inventive process, to affect bone deposition, in a method similar to that reported in PCT Publications WO 98/05318 (Cook, et al.), and WO 98/05319 (Cook, et al.).

The invention encompasses a CLA-containing material, produced by the inventive process, incorporated into an edible fat spread containing from about 0.05 to about 20% by weight of the spread, conjugated linoleic acid residues. In another embodiment the invention contemplates other foods containing CLA, prepared by the process of the invention, similar to those disclosed in PCT Publication WO 97/46118 (Cook, et al.), including for example, a liquid dietetic food for parenteral administration to humans containing emulsified fat particles, a baby formula, or a low-residue liquid enteral dietetic product useful as a high-protein, vitamin and mineral supplement.

Alternatively, a CLA-containing material, prepared by the inventive process, may be provided as a daily ration in a vehicle with a lipid component containing or comprising 0.01 to 10 gram equivalents of the 10,12 isomers, most preferably 0.01 to 10 gram equivalents of the t10, c12 isomer. Gram equivalents means that the total amount of 10,12 isomers provided, irrespective of other isomers present, is from 0.01 to 10 grams. When the 10,12 isomers are provided as part of a daily ration, the intake may occur in a single dose, or as a series of doses in a feed or various food products consumed throughout the day.

The CLA-containing materials produced by the inventive process, and compositions containing such CLA materials, may take the form of a bulk product for sale in commerce. The bulk CLA product contains or comprises at least 50 percent conjugated linoleic acid isomers. The linoleic acid isomers may be characterized in containing greater than 95 percent of a mixture of t10, c12 and c9, t11 isomers. This bulk product may be diluted into nutritional products such as animal feeds, human dietary supplements, and human food products. Those products will be compositions containing or comprising linoleic acid isomers characterized in containing greater than 95 percent of a mixture of t10, c12 and c9, t11 isomers.

The CLA-containing materials of the present invention will have a variety of uses. These uses include: the reduction of body fat in animals; increasing muscle mass in animals; increasing feed efficiency in animals, reducing body weight in humans, attenuating allergic reactions in animals; preventing weight loss due to immune stimulation in animals; elevating CD-4 and CD-8 cell counts in animals; increasing the mineral content of bone in animals; preventing skeletal abnormalities in animals; and, decreasing the amount of cholesterol in the blood of animals. In each case, the term animal includes all mammals including humans. The preferred dosages and ratios of the 10,12 isomers, most preferably the t10, c12 isomer, utilized for each application are the same as described above.

In a preferred embodiment of the present invention, a safe and effective nutritional or therapeutic amount of t10, c12-CLA is orally administered to an animal (including humans) to decrease body weight or fat. In some embodiments, the t10, c12-CLA is at least approximately 80% pure, in other embodiments, the t10, c12-CLA is at least approximately 90% pure, and in still other embodiments, the t10, c12-CLA is at least approximately 95% pure. t10, c12-CLA may be administered to obese and non-obese humans. Because t10, c12-CLA is a non-toxic, naturally occurring food ingredient and not a drug, t10, c12-CLA may be consumed as a part of a normal diet and finds use as a part of everyday nutrition in people without obesity. A nutritionally effective amount is that amount t10, c12-CLA that, when ingested in purified form or as food supplement results in a reduction in body weight or fat without impairing or interfering with proper nutrition. Accordingly, administration of a nutritionally effective amount of t10, c12-CLA achieves weight loss without sensory deprivation associated with reduction in food intake. t10, c12-CLA may also be used to treat humans with slight to profound clinical obesity. When treating humans with clinical obesity, a therapeutically effective amount of t10, c12-CLA is administered. A therapeutically effective amount is that amount which causes a reduction in weight or body fat of a clinically obese person. In the present invention, about 0.1 to 15 grams of CLA may be administered per day, preferably about 0.1 to 5 grams per day may be administered and most preferably about 1.8 grams per day may be administered. In general, the amount of CLA administered is not critical as long as it is enough to be nutritionally or therapeutically effective. The amounts of CLA deemed nutritionally or therapeutically effective are those which result in measurable weight or fat loss when administered over a four week period or longer.

The present invention also contemplates the use of derivatives of the isomer-enriched preparation of CLA. For example, CLA may be free or bound through ester linkages or provided in the form of an oil containing isomer enriched CLA triglycerides. In these embodiments, the triglycerides may be partially or wholly comprised of isomer enriched CLA attached to a glycerol backbone. The isomer enriched CLA may also be provided as a methylester or ethylester. Furthermore, the isomer enriched CLA may be in the form of a non-toxic salt, such as a potassium or sodium salt (e.g., a salt formed by reacting the CLA with an alkali hydroxide).

A CLA-containing material produced by the inventive process may be administered orally. The isomer enriched CLA may be formulated with suitable carriers such as starch, sucrose or lactose in tablets, pills, dragees, capsules, solutions, liquids, slurries, suspensions and emulsions. The isomer enriched CLA may be provided in aqueous solution, oily solution, as or in any of the other forms discussed above. The tablet or capsule of the present invention may be coated with an enteric coating which dissolves at a pH of about 6.0. to 7.0. A suitable enteric coating which dissolves in the small intestine but not in the stomach is cellulose acetate phthalate. In a preferred formulation, the isomer enriched CLA is provided as soft gelatin capsules. The isomer enriched CLA may also be provided by any of a number of other routes, including, but not limited to, intravenous, intramuscular, intra-arterial, intramedullary, intrathecal, intraventricular, transdermal, subcutaneous, intraperitoneal, intranasal, enteral, topical, sublingual or rectal means. Further details on techniques for formulation for and administration and administration may be found in the latest edition of Remington's Pharmaceutical Sciences (Maack Publishing Co., Easton, Pa.).

The isomer enriched CLA produced by the inventive process may also be provided as a supplement in various prepared food products and drinks. For the purposes of this application, prepared food product means any natural, processed, diet or non-diet food product to which isomer enriched CLA prepared by the inventive process has been added. The isomer enriched CLA may be added in the form of free fatty acids or as an oil containing partial or whole triglycerides of isomer enriched CLA. Therefore, isomer enriched CLA may be directly incorporated into various prepared food products, including, but not limited to diet drinks, diet bars, supplements, prepared frozen meals, candy, snack products (e.g., chips), prepared meat products, milk, cheese, yogurt and any other fat or oil containing foods.

A CLA-containing material prepared by the inventive process, as with other CLA materials, is susceptible to oxidation. Therefore it is desirable to package isomer enriched CLA for human use with suitable antioxidants such as lecithin, tocopherols, ascorbate, ascorbyl palmitate or spice extracts such as rosemary extract.

All documents, e.g., patents and journal articles, cited above or below are hereby incorporated by reference in their entirety. In the following examples, all amounts are stated in percent by weight of active material unless indicated otherwise. One skilled in the art will recognize that modifications may be made in the invention without deviating from the spirit or scope of the invention. The invention is illustrated further by the following examples which are not to be construed as limiting the invention or scope of the specific procedures or compositions described herein. All levels and ranges, temperatures, results etc., used herein are approximations unless otherwise specified. The following examples exemplify the advantages of the invention.

EXAMPLES

Example 1

Preparation of Conjugated Linoleic Acid Methyl Ester (CLME) using Potassium Methoxide Methyl esters derived from safflower oil (600.7 g, 2.04 moles) were treated with a 25% solution of potassium methoxide in methanol (48.4 g, 12.1 g potassium methoxide contained, 2 wt % based on the weight of the methyl esters) at 110° C. After completion of the conjugation reaction, the fatty acid distribution (as determined by GC) was CLMEs: 78.3%; linoleic esters: 0.4%; oleate esters: 14.5%; stearate esters: 2.5%; palmitate esters: 3.3%.

Example 2

Preparation of CLME using Potassium Isopropoxide

Methyl esters derived from safflower oil (151.0 g, 0.513 mol) were treated with a 20% solution of potassium isopropoxide in isopropanol (43.4 g, 0.0884 moles potassium isopropoxide, 5.7 wt % based on the weight of the methyl esters) at 130° C. After completion of the conjugation reaction, the fatty acid distribution (as determined by GC) was CLMEs: 74.1%, linoleic esters: 1.1%, oleate esters: 17.1%, stearate esters: 1.7%, palmitate esters: 3.6%.

Example 3

Saponification of CLME in Agueous KOH in the Presence of Preformed Potassium Linoleate Potassium hydroxide solution (14.07 g, 45% KOH, 0.113 moles) was diluted in water (180.02 g). Next, preformed potassium salt of conjugated linoleic acid (CLA) (3.06 g, 0.0109 moles) was added. The base solution was heated to 70° C. and CLME (14.11 g, 0.0479 moles) was added in one portion. An opaque mixture was formed. After 4 hours at 70° C. the clear yellow solution was sampled and analyzed by gas chromatography. Residual CLME was found to be 4.5% by GC.

Example 4

Saponification of Conjugated Linoleic Acid Methyl Ester (CLME) in Aqueous KOH in the Absence of Preformed Potassium Linoleate Potassium hydroxide solution (14.02 g, 45% KOH, 0.112 moles) was diluted in water (180.33 g). The base solution was heated to 70° C. and CLME (17.35 g, 0.0589 moles) was added in one portion. An opaque mix formed. After 4 hours at 70° C. the cloudy mix was sampled and analyzed by gas chromatography. Residual CLME was found to be 47.2% by GC.

Example 5

Saponification of CLME with Sodium Hydroxide in Aqueous Alcohol

CLME (50.13 g, 0.170 moles), water (50.21), ethanol (51.04 g) and sodium hydroxide (9.54 g, 0.238 moles) were combined and heated to 50–55° C. After one hour no residual CLME was detectable.

Example 6

Saponification of CLME with Alcoholic KOH

Butanol (121.6 g) and KOH (45% aqueous solution, 24.53 g, 0.197 moles) were combined and heated. Water was removed azeotropically and collected in a Dean-Stark trap. After drying, the solution was cooled to 60–65° C. CLME (16.22 g, 0.0551 moles) was added in one portion. A precipitate formed quickly. The slurry was held at 60° C. for 2.5 hours. The off-white solid was collected via filtration. The solid was taken up in water (100 mL) and the solution was brought to a pH of 4 with phosphoric acid. The aqueous phase was drained and the organic phase was washed with another 50 mL of water. The organic phase was recovered and dried yielding clear oil.

Example 7

Continuous Neutralization of Salt Slurry

To a CLA soap slurry (46% potassium salt of CLA; feed rate 209.0 lb/hr) was added phosphoric acid ($H_3PO_4$, 85% solution; (feed rate 56.4 lb/hr)). Operating conditions were average slurry temperature: 95.5° F.; average recycle ratio: 17 at 7.7 gpm circulation rate; average loop circulation rate: 7.7 gpm at 90% motor speed; loop 1 change over time: 29 minutes; loop pressure: 10 psig with control valve 15% open. Theoretical CLA production rate was 84.6 lb/hr. Actual recovery rate was 92% of the theoretical value. The recovered CLA met the GC and acid value (AV) specifications (AV: 201.1, specification range: 195–204).

The invention is now described in such full, clear, concise and exact terms as to enable any person skilled in the art to which it pertains, to practice the same. It is to be understood that the foregoing describes preferred embodiments of the invention and that modifications may be made therein without departing from the spirit or scope of the invention as set forth in the claims. A person of ordinary skill in the art will also understand that besides manufacture of the desired CLA product, the invention can be used to recover fatty acids from corresponding esters, isomerize unsaturation in aliphatic compounds, and reduce formation of undesired isomers in long chain polyunsaturates.

What is claimed is:

1. A process to produce a conjugated linoleic acid-containing material, comprising:
    isomerization of an alkyl ester of a linoleic acid-containing material to a conjugated linoleic acid-containing fatty acid ester,
    saponification of said fatty acid ester to a conjugated linoleic acid-containing fatty acid salt wherein said step of saponification is performed in a $C_1$–$C_4$ aliphatic mono-alcohol solvent at or below 100° C. and, optionally,
    neutralization of said fatty acid salt with an acid source to produce a conjugated linoleic acid-containing fatty acid.

2. A process according to claim 1, wherein said step of isomerization is catalyzed by a catalyst in a nonaqueous system, and said catalyst is a base.

3. A process according to claim 2 wherein said catalyst is an alkali or alkaline earth alkoxide salt of a $C_1$–$C_4$ alkyl group alcohol.

4. A process according to claim 3 wherein the cation of said alkoxide salt is sodium, potassium or calcium.

5. A process according to claim 3 wherein said catalyst is delivered as a solid or a solution in a conjugate alcohol of said alkoxide.

6. A process according to claim 1, wherein said step of isomerization is performed at or below 140° C.

7. A process according to claim 1, wherein said step of isomerization is performed between 90–130° C.

8. A process according to claim 1, wherein said step of isomerization is performed between 110–120° C.

9. A process according to claim 2 wherein said catalyst is added to said alkyl ester at or below 140° C.

10. A process according to claim 1, wherein said step of saponification is performed between ambient temperature and 100° C.

11. A process according to claim 1, wherein said step of saponification is performed with an inorganic or alkyl ammonium hydroxide.

12. A process according to claim 11 wherein the cation of said hydroxide is selected from the group consisting of sodium, potassium and calcium or from the group consisting of symmetrical tetra $C_1$–$C_4$ alkyl, benzyl tri $C_1$–$C_4$ alkyl, dibenzyl di $C_1$–$C_4$ alkyl and long chain $C_{12}$–$C_{18}$ alkyl tri $C_1$–$C_4$ alkyl ammonium groups.

13. A process according to claim 1, wherein said step of saponification is effected by the use of a base consisting of an alkali, alkaline earth or alkyl ammonium cation and a hydroxide, bicarbonate or carbonate anion.

14. A process according to claim 13 wherein said cation of said base is selected from the group consisting of sodium, potassium and calcium or from the group consisting of symmetrical tetra $C_1$–$C_4$ alkyl, benzyl tri $C_1$–$C_4$ alkyl, dibenzyl di $C_1$–$C_4$ alkyl and long chain $C_{12}$–$C_{18}$ alkyl tri $C_1$–$C_4$ alkyl ammonium groups.

15. A process to produce a conjugated linoleic acid-containing material, comprising:
    isomerization of an alkyl ester of a linoleic acid-containing material to a conjugated linoleic acid-containing fatty acid ester,
    saponofication of said fatty acid ester to a conjugated linoleic acid-containing fatty acid salt, wherein said step of saponification is performed in an aqueous system at or below 100° C. and a preformed alkali, alkaline earth, or alkyl ammonium salt of said conjugated linoleic acid-containing fatty acid is present and, optionally,
    neutralization of said fatty acid salt with an acid source to produce a conjugated linoleic acid-containing fatty acid.

16. A process according to claim 15 wherein the cation of said preformed salt is selected from the group consisting of sodium, potassium and calcium or from the group consisting of symmetrical tetra $C_1$–$C_4$ alkyl, benzyl tri $C_1$–$C_4$ alkyl, dibenzyl di $C_1$–$C_4$ alkyl and long chain $C_{12}$–$C_{18}$ alkyl tri $C_1$–$C_4$ alkyl ammonium groups.

17. A process to produce a conjugated linoleic acid-containing material, comprising:
    isomerization of an alkyl ester of a linoleic acid-containing material to a conjugated linoleic acid-containing fatty acid ester, saponification of said fatty acid ester to a conjugated linoleic acid-containing fatty acid salt, wherein said step of saponification is performed in a mixed aqueous/$C_1$–$C_4$ alkyl mono-alcohol system at or below 100° C., isolation of said conjugated linoleic acid-containing fatty acid salt and, optionally, neutralization of said fatty acid salt with an acid source to produce a conjugated linoleic acid-containing fatty acid.

18. A process according to claim 17 wherein the cation of said fatty acid salt is selected from the group consisting of sodium, potassium and calcium.

19. A process according to claim 1 wherein said fatty acid salt is isolated.

20. A process according to claim 19 wherein the cation of said fatty acid salt is selected from the group consisting of sodium, potassium and calcium.

21. A process according to claim 1, wherein said acid source is selected from the group consisting of sulfuric, phosphoric, citric, hydrochloric and oxalic acids.

22. A process according to claim 1, wherein said step of neutralization is performed in a continuous neutralizing apparatus.

23. A process to produce a conjugated linoleic acid-containing material, comprising:

isomerization of an alkyl ester of a linoleic acid-containing material to a conjugated linoleic acid-containing fatty acid ester, saponification of said fatty acid ester to a conjugated linoleic acid-containing fatty acid salt, refinement of said fatty acid salt by selective precipitation of long chain $C_{14}$–$C_{20}$ fatty acid salts from a solution in an alcoholic or aqueous/alcoholic solvent and, optionally, neutralization of said fatty acid salt with an acid source to produce a conjugated linoleic acid-containing fatty acid.

24. A process according to claim 23 wherein the cation of said fatty acid salt is selected from the group consisting of sodium, potassium or calcium.

25. A process according to claim 23 wherein said alcoholic solvent is selected from the group consisting of aliphatic short chain $C_1$–$C_4$ mono alcohols and a combination thereof.

26. A process according to claim 15, wherein said step of isomerization is catalyzed by an alkali or alkaline earth alkoxide salt of a $C_1$–$C_4$ alkyl group alcohol.

27. A process according to claim 17, wherein said step of isomerization is catalyzed by an alkali or alkaline earth alkoxide salt of a $C_1$–$C_4$ alkyl group alcohol.

28. A process according to claim 23, wherein said step of isomerization is catalyzed by an alkali or alkaline earth alkoxide salt of a $C_1$–$C_4$ alkyl group alcohol.

* * * * *